United States Patent [19]

Marinaccio et al.

[11] Patent Number: 5,131,844
[45] Date of Patent: Jul. 21, 1992

[54] CONTACT DIGITIZER, PARTICULARLY FOR DENTAL APPLICATIONS

[75] Inventors: Paul J. Marinaccio, East Orleans; Bruce Nappi, Reading; Khushroo M. Captain, Cambridge; Alan J. Lane, Lexington, all of Mass.

[73] Assignee: Foster-Miller, Inc., Waltham, Mass.

[21] Appl. No.: 682,001

[22] Filed: Apr. 8, 1991

[51] Int. Cl.$^5$ .............................................. A61C 19/04
[52] U.S. Cl. ..................................... 433/72; 128/776; 33/503; 33/513
[58] Field of Search ............... 433/72, 75, 76; 409/92, 409/126, 98, 99, 103, 114, 121, 124; 364/474.03, 474.29; 33/503, 504, 513, 514; 128/776

[56] References Cited

U.S. PATENT DOCUMENTS

| | | | |
|---|---|---|---|
| 1,387,329 | 8/1921 | Stark | 433/76 |
| 4,575,805 | 3/1986 | Moermann et al. | 364/474 |
| 4,997,369 | 3/1991 | Shafir | 433/72 |
| 5,017,139 | 5/1991 | Mushabac | 433/72 |

FOREIGN PATENT DOCUMENTS

| | | |
|---|---|---|
| 0040165 | 11/1981 | European Pat. Off. . |
| 0091876 | 10/1983 | European Pat. Off. . |
| 0110797 | 6/1984 | European Pat. Off. . |
| 1194061 | 5/1959 | France . |
| 75885 | 7/1961 | France . |
| 157456 | 1/1962 | U.S.S.R. . |
| 2140308 | 11/1984 | United Kingdom ............... 433/75 |

OTHER PUBLICATIONS

Brochure, "Announcement-Procera Station Installed", Nobelpharma, Feb. 1991.
Brochure, "DCS—Titansystem Dux 1", Gim-Alldent, Germany.
Matts Andersson et al., "Clinical results with titanium crowns fabricated with machine duplication and spark erosion", Acta Odontol Scand 47, pp. 279-286 (1989).
Brochure, "Capture 3-Dimensional Position Data Instantly From Any Object—The Perceptor", Micro Control Systems, Inc.

*Primary Examiner*—Cary E. O'Connor
*Attorney, Agent, or Firm*—Ostrolenk, Faber, Gerb & Soffen

[57] ABSTRACT

A dental surface tracer includes a probe with a tip that can be moved to trace a given dental surface, including a mounting device for mounting the tracer to a stable reference location and defining a base plane; a first plurality of links which are substantially coplanar and define a plane of movement; the links being pivotably attached to the mounting device so that the plane of movement makes a variable angle with the base plane; a distal one of the first plurality of links being movable in two dimensions within the plane of movement; circuitry for generating electrical signals representative of movements of the probe tip, as a function exclusively of movements of the first plurality of links; a dental handpiece supporting the probe; and a second plurality of links which hold the handpiece and are attached to the first plurality of links; the second plurality of links holding the probe tip at all times at a fixed location in the plane of movement with respect to the distal link of the first plurality of links; and permitting the handpiece to move about three axes without moving the probe tip from the fixed location. The entire tracer exclusive of the handpiece is sized to be accommodated within the human mouth.

31 Claims, 7 Drawing Sheets

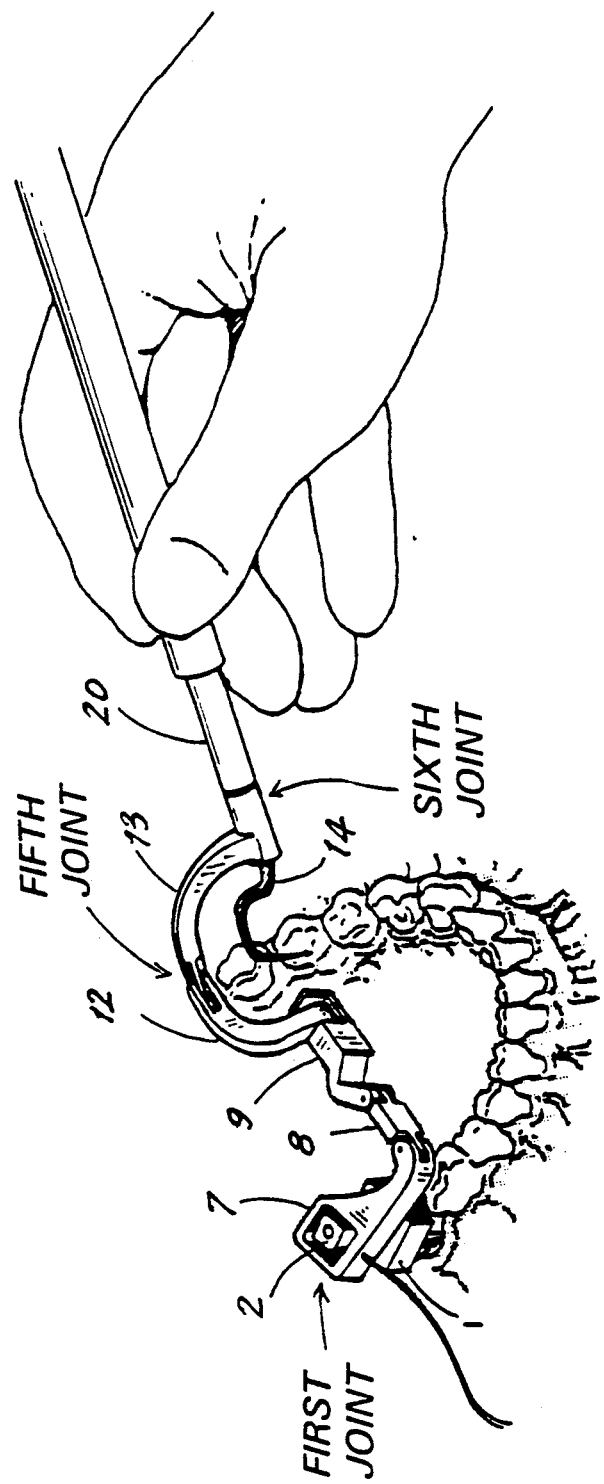

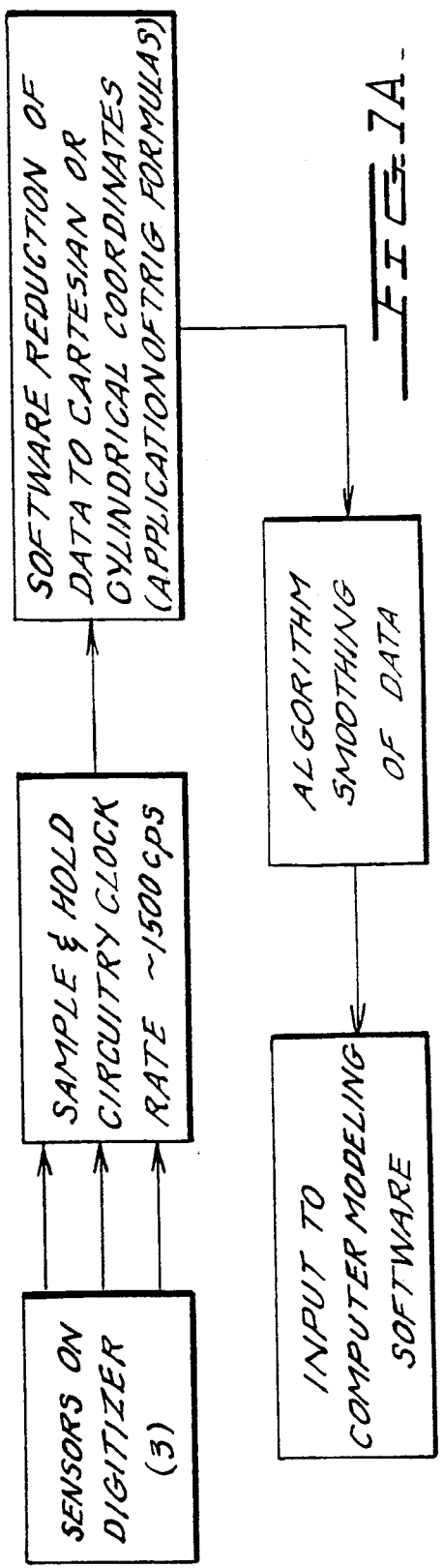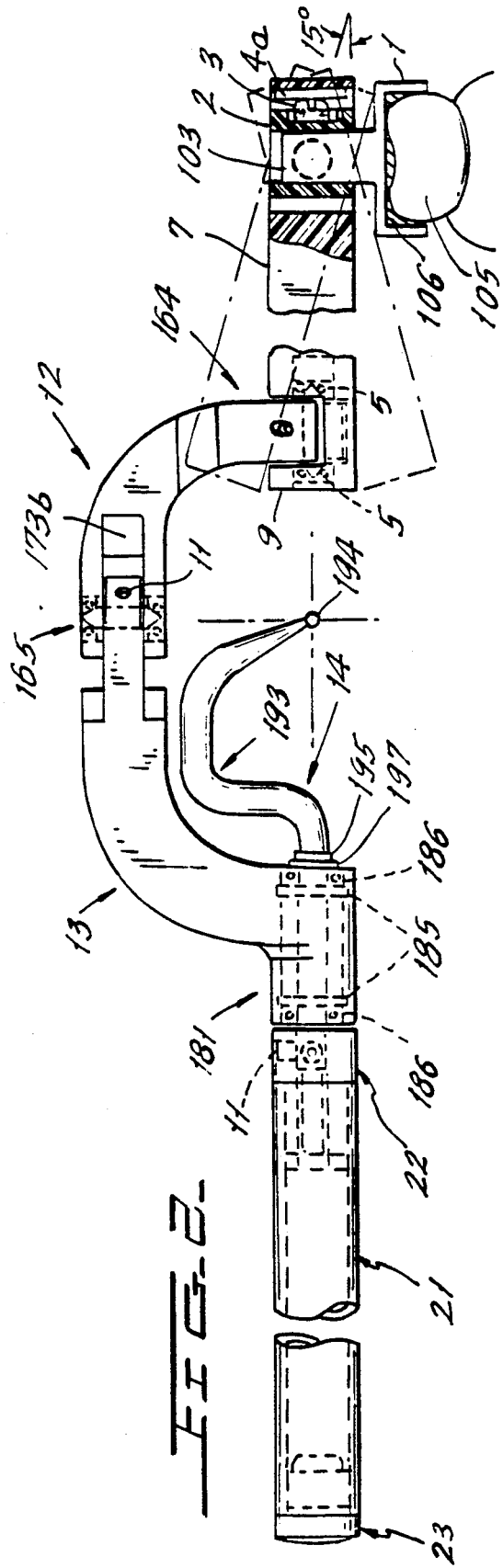

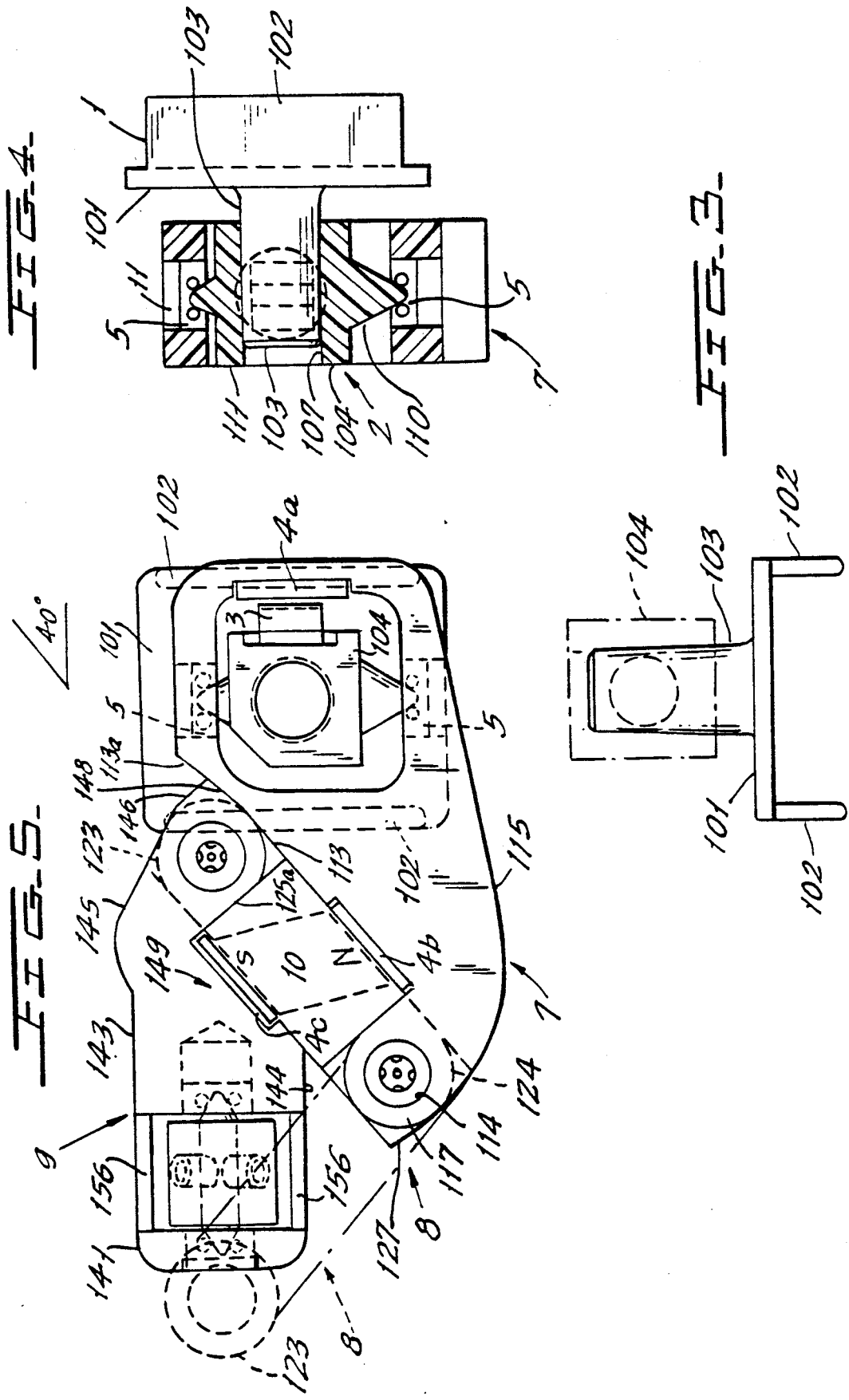

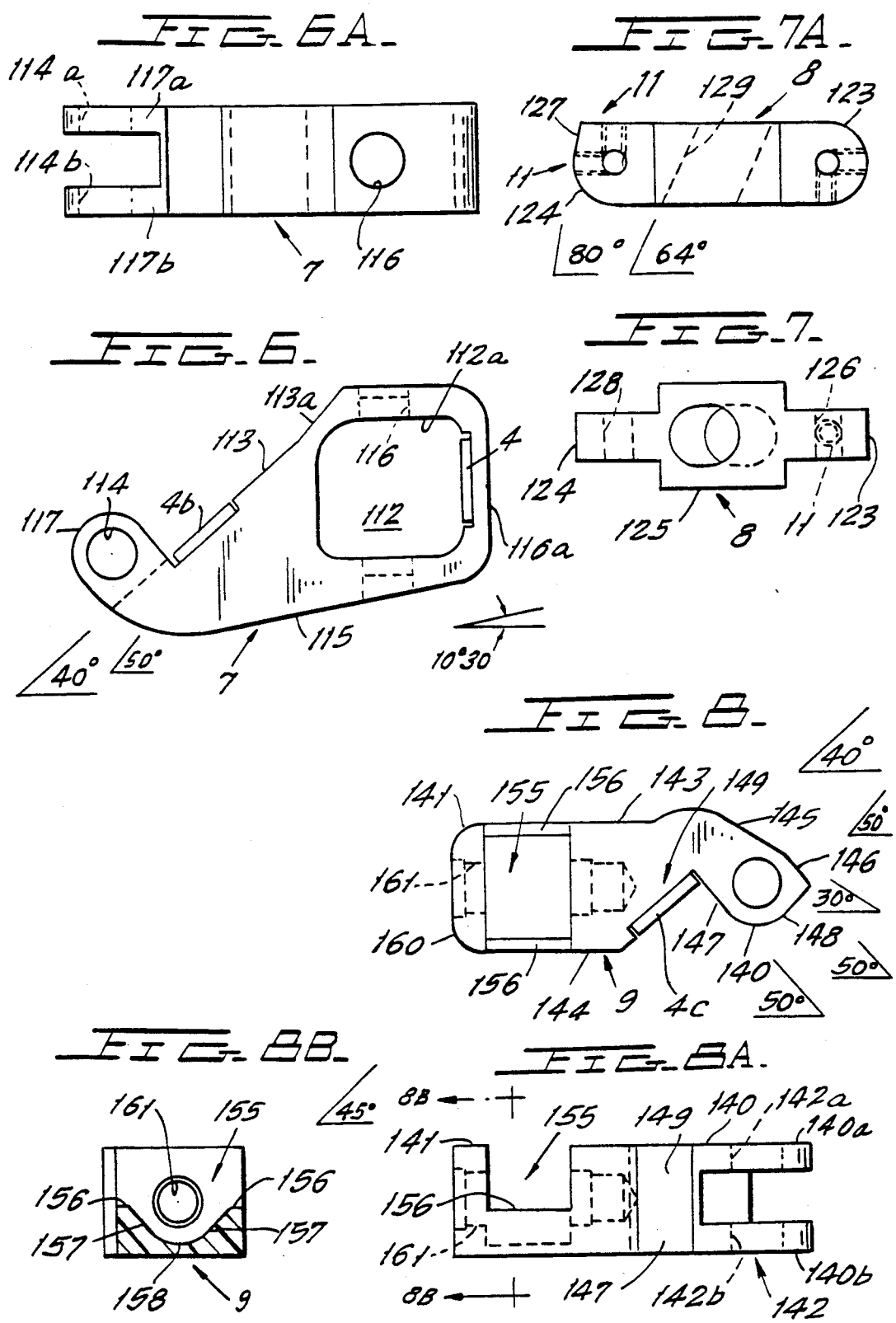

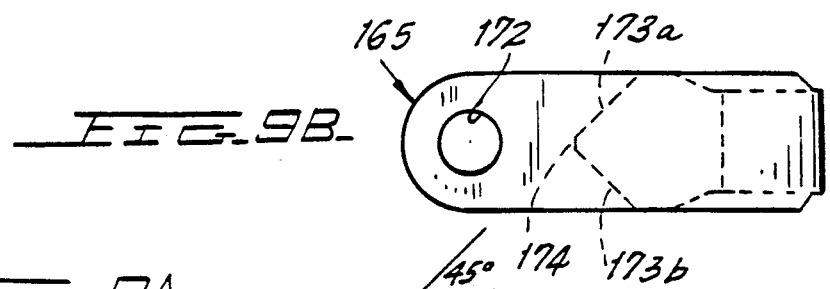
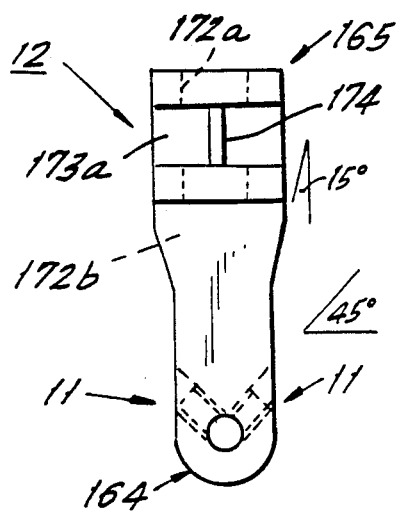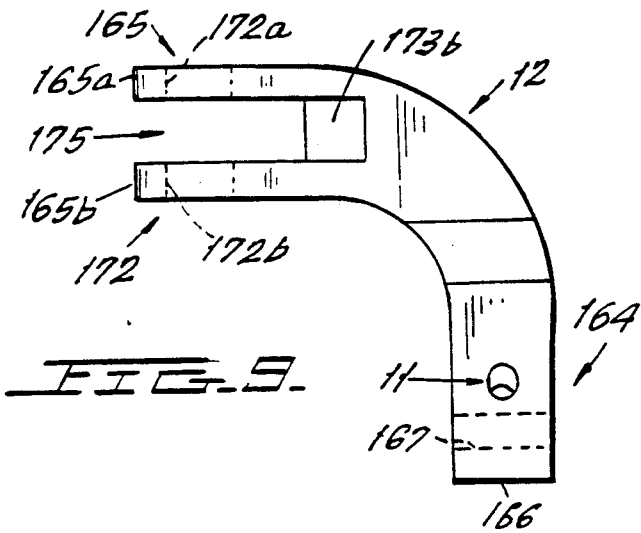
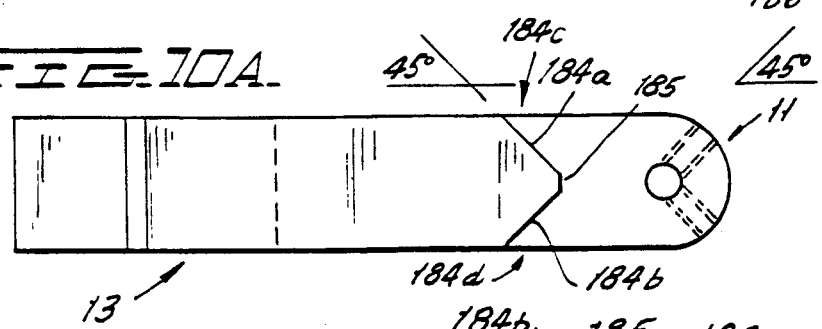
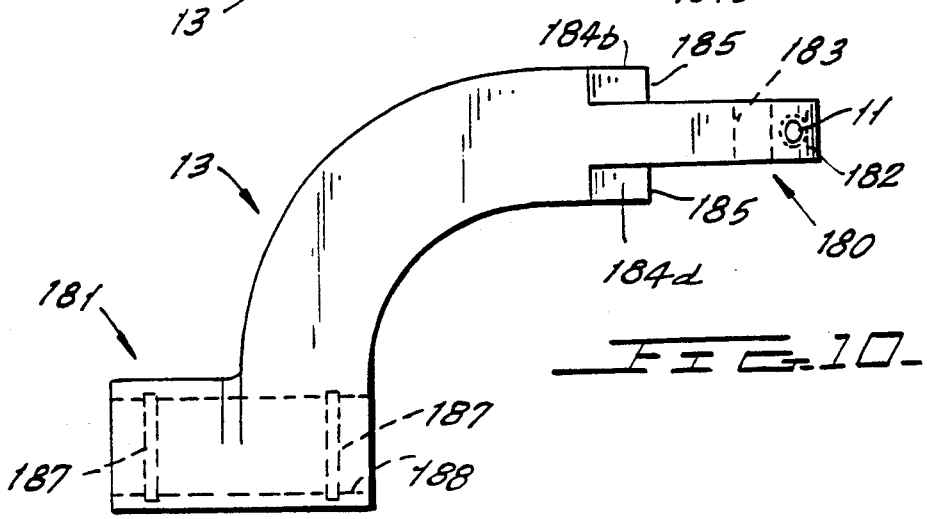

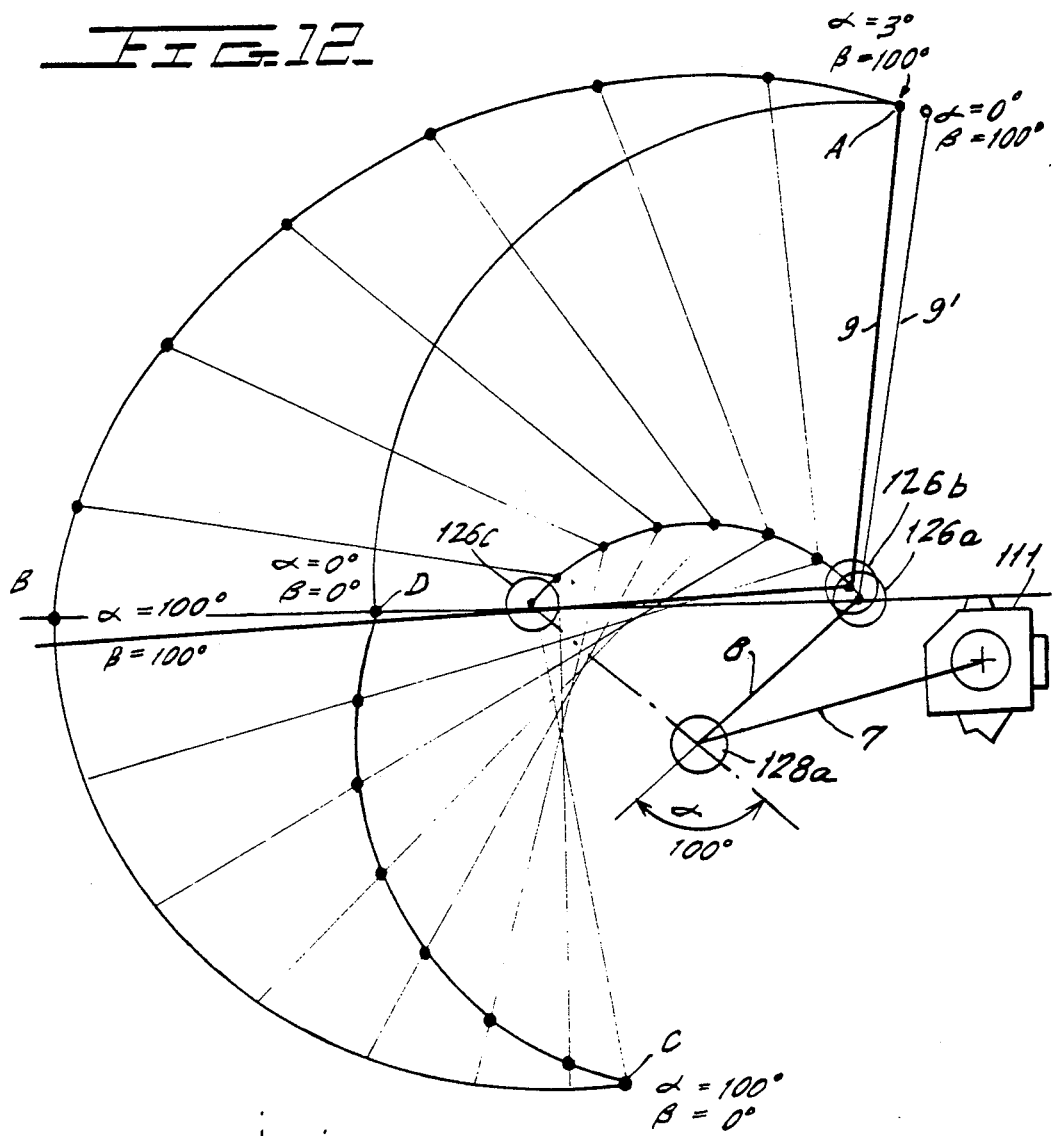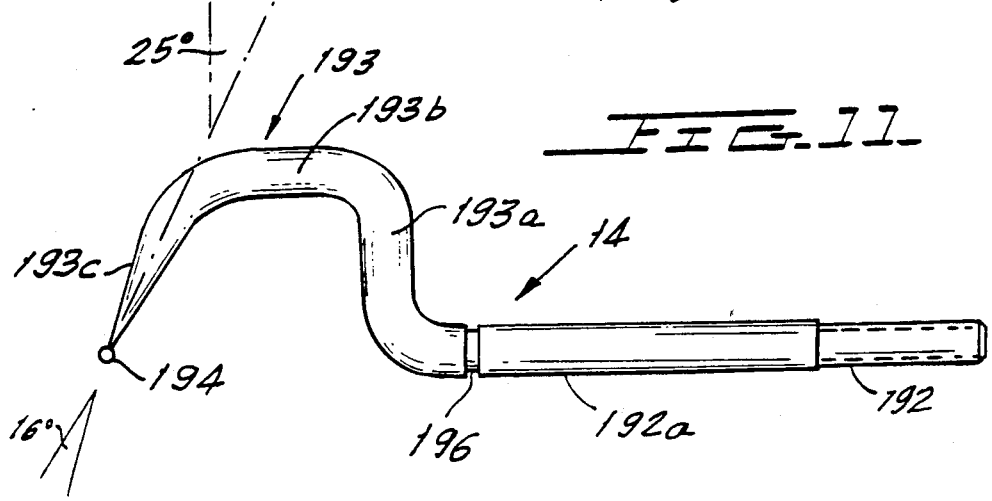

CONTACT DIGITIZER, PARTICULARLY FOR DENTAL APPLICATIONS

STATEMENT AS TO RIGHTS TO INVENTIONS MADE UNDER FEDERALLY-SPONSORED RESEARCH AND DEVELOPMENT

The United States has certain rights in this invention under the terms of Grant No. 1 R43 DEO7835-01 and Grant No. 2 R44 DEO7835-02 awarded by the National Institute of Dental Research (National Institutes of Health).

CROSS-REFERENCE TO RELATED APPLICATIONS

This application is related to U.S. patent application Ser. Nos. 07/364,017 (Rekow et al.); 07/364,270 (Riley et al.); 07/365,139 (Riley et al.); and 07/365,140 (Erdman et al.); all filed Jun. 9, 1989, which are expressly incorporated by reference herein.

BACKGROUND OF THE INVENTION

1. Field of the Invention

The invention relates to a probe system including an electromechanical digitizer, which can be traced over a surface for generating digital data representative of the configuration of such surface. A primary application of the digitizer is contemplated to be digitizing dental surfaces, either within the oral cavity, or outside the oral cavity, for example in a dental laboratory.

It is expected that the data generated by the digitizer will be used with suitable computer modeling (e.g., line modeling, surface-skin modeling, or solids modeling) and computer-aided design techniques in various dental applications, such as orthodontics, prosthodontics and other restorative dentistry, forensics, and teaching.

2. Background Art

The application of computer modeling and mechanical contact digitizing to dentistry is new and is yet unproven from a practical standpoint.

General Commercial Digitizers

Three-dimensional digitizing devices have become common in the past few years and are used in the aircraft, automotive, industrial and leisure fields. These are divided roughly into four areas:
Mechanical contact
Magnetic
Ultrasonic
Digital imaging.

It appears that a mechanical contact system will be most workable in the dental field and will entail minimal changes in dental practices and the required level of dental skill.

Microcontrol Systems (Vernon, Conn.) has introduced a mechanical contact 3-D digitizer called the Space Tablet and the Perceptor 3-D. In operation, the stylus at the end of the Perceptor's arm is tracked over the solid object. Movement about 6 axes appears to be provided. A precision potentiometer housed in the extension arm computes the (x,y,z) coordinates of any position based on the angle of rotation and known arm length. As many as seven points per second can be recorded. In addition, four different digitization modes are switch selectable and resolution ranges between 0.007 and 0.010 in.

Unfortunately, this commercial system is not suitable for use in the dental environment.

Mechanical Dental Systems

U.S. Pat. No. 4,182,312 is directed to a dental probe mechanism in which three-dimensional information is provided by a transducer mechanism connected to the probe. The probe has limited maneuverability and so cannot be used to noninvasively detect the contours of many tooth portions that are not readily accessible.

Additional linkages and dental equipment of background interest are disclosed in the following U.S. patents:

| | | |
|---|---|---|
| 1,230,156 | 1,387,329 | 1,799,528 |
| 1,831,390 | 2,119,823 | 2,119,824 |
| 2,299,151 | 2,447,287 | 2,566,903 |
| 2,701,915 | 2,841,871 | 3,035,348 |
| 3,063,149 | 3,152,401 | 3,218,624 |
| 3,226,828 | 3,254,413 | 3,380,163 |
| 3,490,146 | 3,564,717 | 3,777,740 |
| 3,943,913 | 3,943,914 | 4,085,514 |
| 4,344,755 | 4,390,028 | 4,402,326 |
| 4,445,857 | 4,495,952 | 4,634,377 |
| 4,639,220 | | |

See also U.S.S.R. Patent 157,456, French Patent of Addition 75,885, and French Patent 1,194,061.

Optical Dental Systems

The present inventors are aware of work in this field performed in France and the United States by Francois Duret. He has filed European and United States patent applications on imaging devices (EP 0 040 165-A1; EP 0 091 876-A1; and EP 0 110 797-A1) and sparse references have occurred in the trade journals to his work. His imaging device consists of a miniature black and white camera which obtains multiple views of the oral cavity.

The Duret system has attempted to automate the production of restorations from obtaining the impression to producing the prosthesis. It is said to be capable of several functions:

To produce a numerical data set that characterizes tooth or preparation surfaces by a nontraumatic, noncontact optical probe.

To present the tooth image in graphic form on a workstation allowing an operator to modify the model dynamically.

To convert the surface data into a form which can direct an automatic milling machine to cut the form in a ceramic, restorative or biocompatible material.

To measure the contours of the surface of a tooth or preparation, a pattern of alternating black and white lines is projected onto the surface. The pattern is viewed with a miniature TV camera from an angle away from the axis of projection of the lines. This allows surface relief to be measured.

While the theory is straightforward, the implementation is very complex and not yet practical. Duret claims to have spent 7 years or more, working out this aspect of the system. It is the most difficult part of the system and requires a large computer to process the data. Some of the complications are:

The teeth must be coated to obtain a consistent color.

The surrounding soft tissues must be retracted to visually expose the marginal portions of the teeth.

Multiple images are required to observe all of the surfaces. The program must in fact compute surface segments and then link them together appropriately, removing any overlaps.

The occlusal surface must be digitized with the jaws apart to allow the camera to fit. A calculation must be made to estimate where the occlusion will actually occur when the jaw is closed.

To obtain sufficient resolution, it is believed each surface image must be viewed multiple times with the projected lines moved slightly so that a line edge is viewed every 25 microns across the surface. On this assumption, using lines 1 mm wide, spaced 1 mm apart (with the camera 2 cm from the surface), 40 separate images would be required to obtain the 25 microns of spacing.

The system cannot handle visual artifacts such as reflections from saliva, poor line reflectivity on the skin, and line discontinuity near abrupt morphology.

The calculations required to produce a suitable data set to use in the next step of the process take approximately 2 min on a VAX computer running with 5 Mb core memory and 80 Mb hard disk. A library of stored tooth forms is used to generate the outer contour for missing teeth. This library is also used to help bound the range of surface locations which can be taken by the data. The dentist must select an appropriate tooth model from the library to work with.

Once a tooth surface is determined, the surface is displayed in wire-mesh form on a workstation. The operator must then make decisions on the appropriateness of the model and make size, scaling and other changes where necessary. One of the areas requiring modeling is the occlusal surface. Another is surface element matching errors. Edge contouring may be required to avoid false sharp ridges.

The completed computer model is used to generate a tool path data file for a particular machine and set of cutting tools (a Hennson miller with automatic tool changer is used in Duret's system). The milling machine then cuts a restoration. It typically takes 30 min to produce the raw tooth. A trained dental technician then hand-polishes and colors the machined restoration. This system appears to be unable to accomplish complete automation in an expeditious and cost-effective manner.

Accordingly, it would be desirable to overcome the following disadvantages of the Duret system:

The surface generation software should be simplified by providing a fixed reference point for digitizing a given tooth.

The software should be able to run on a smaller computer.

The surface generation software should be simplified by allowing each data point for the surface to be read directly from the digitizer sensors and not to require computation from multiple photo projections.

The sampled data should be usable to form a continuous surface and not require piecing segments together.

Redundant data should not be collected, thereby reducing memory requirements, preferably by coordination of surface contact data, quantizing the resolution of the accepted data, and real time sensor data processing. These measures would permit storing only needed data.

The contact probe should not be affected by reflections from saliva or tooth transparency.

The contact probe should be able to sense below the gum surface where the cameras cannot see.

The contact probe should be able to reach surfaces that are always shadowed from view by surrounding teeth.

Other Optical Systems

U.S. Pat. No. 4,575,805 discloses a system that is said to optically scan a dental surface, digitize and record its contour data, determine the necessary shape of a corresponding dental implant, and then control a process for manufacturing the implant.

Additional video systems of background interest are disclosed in U.S. Pat. Nos. 3,861,044; 4,324,546; 4,611,288; 4,663,720; and 4,742,464.

All prior art mentioned herein is expressly incorporated by reference.

None of the prior art disclosed above addresses the specific dental applications we have identified, and more specifically, the digitizing system proposed herein.

OBJECTS OF THE INVENTION

This invention relates to a mechanical digitizer, particularly for use in the fields of restorative dentistry, forensic dentistry, orthodontics, and the teaching of dentistry practices.

Restorative Dentistry—Current restorative techniques in crown and bridge fabrication involve tooth preparation, impression procedures, construction of the restoration, and its insertion.

Tooth preparation with exact replication of a die is the key to an accurately fabricated restoration. Currently, the state-of-the-art involves preparation of a tooth by a clinician, with subsequent gum retraction. The geometry of the preparation is then captured with impression material. These procedures lead to the making of a die, which in turn is processed to wax a restoration that is ultimately cast and sometimes veneered to aesthetically match the surrounding environment.

Impression techniques are inconvenient, tedious, time-consuming, and, in general, unpleasant for the patient. Sometimes the making of an impression is not possible in certain individuals due to a highly sensitive gag reflex. The production of a highly accurate die is time-consuming and difficult to accomplish. For example, the dimensions of the die vary with the nature and type of impression material and the stone that is used. Mixing of impression material and timing of the pouring of the impression are other critical factors that influence die accuracy. All impressions are manually done and are subject to human working error. At times, impressions need to be repeated, especially if care is not exercised initially in retraction and tissue control. Simplifying these procedures while maintaining or improving upon their accuracy would be highly desirable and contribute beneficially to both the dentist and the patient. In addition, if these methods could improve restoration production, they would be widely embraced. Of even more importance is the fact that gingival retraction procedures may traumatize the gingival tissues, lead to gum recession, and result in a lack of definition of the marginal finish line as captured by the impression.

The ability to digitize soft and hard tissues presents potential applications in other areas of dentistry and medicine where the use of impression-taking procedures is currently disadvantageous or impossible:

Oral Surgery—The impression-taking process in oral surgery procedures involving prosthetic appliance fabrication (implants, for example) for the maxilla or mandible is one example. It is very difficult to obtain a good bone impression of the mandible due to tissue management problems, whereas digitization of the mandible may be obtained with little difficulty once the tissue is exposed.

Forensic Applications—The oral cavity geometry, especially the occlusal surface, can be used for identification purposes and is believed to be as unique for each individual as a fingerprint. A digitizing device can be used to create a computer data base from which a visual output can be generated. A quantitative comparison of geometry is possible via numerical methods, allowing the data base to be compared with any other data generated in the future, making exact identification possible simply from a comparison of geometric detail of intact enamel and its interruption with restorations. The ability to capture the oral geometry via digitization and to make quantitative comparisons from that geometry offers an increase in the reliability and speed with which identifications can be made from dental information.

Orthodontic Applications—A geometric data base of the oral cavity has many applications in orthodontics. Orthodontic applications are especially advantageous because of the desirability of having a quantitative data base from which changes over time can be determined. A quantitative geometric data base and the ability to generate three-dimensional displays and manipulate those displays will give the orthodontist capabilities that are not currently available. The visual display can be used to show before-and-after effects. The geometry can be tracked over time to show movement effects and to identify gumline changes, etc. More quantitative measurements and comparisons are possible than with present methods.

A digital description of the oral cavity, using a mechanical digitizing device, will have a major, if not revolutionary, impact on the procedures used for the diagnosis and treatment of orthodontic patients. The mechanical digitizing device can capture (x,y,z) coordinates by point-to-point measurements of the oral cavity for manipulation by computer solids or surface modeling techniques. It will be possible, in real-time, to produce a visual computer model of a patient's teeth in full color and in three dimensions. This model can then be rotated in space, viewed from all angles, expanded, and in general, manipulated by the orthodontist in much the same way as a study model is today. The system will detect changes in tooth position much earlier than with traditional methods. In time these methods may actually replace study models as the primary reference for patient treatment. The orthodontist may in the future actually demonstrate the facial effects of treatment and show the patient before and after images of the tooth positions and resulting facial changes.

The significance of an accurate digital description of the oral cavity for orthodontic applications cannot be overemphasized. Present methods generally involve full face x-rays and measurements of relative tooth positions from these images. The orthodontist presently uses this information and clinical experience and judgment to generate a treatment schedule for the repositioning of each tooth. This involves precise bracket location and periodic follow-up during the course of treatment.

The digital data will allow a precise model of the oral cavity to be produced mathematically and to be visually generated by computer solids or surface modeling techniques. With this model available, the precise relative position of each tooth is known exactly along with the geometric data concerning the meshing of the occlusal surfaces, the resulting bite positions, and the geometrically allowed range of comfortable bite positions. This will allow new diagnostic and treatment methods for orthodontics including temporal mandibular joint (TMJ)-related problems. Since these digital data are mathematically and geometrically precise, they can be used in new ways.

The orthodontic methods disclosed herein will allow several significant improvements. First, the visual model produced can be used to assess the present situation by allowing the dentist to view the entire cavity and each tooth position from many angles. Secondly, it will be possible to recalculate and redisplay each tooth position based on the treatment prescribed, prior to any work on the patient. This will allow the dentist to try out a proposed treatment and alter it before any actual treatment. Furthermore, the optimum placement of each tooth can be calculated for a given aesthetic effect and to efficiently maximize the spatial distribution of teeth in the cavity to obtain the best functional result. In addition, since the precise geometry is known beforehand and the relative tooth positions can be determined with each subsequent visit, it will be possible to quantitatively follow, for example, relative tooth positions, or the location of periodontal disease, over time, and to calculate and display by computer any modification to the treatment schedule.

One of the most important decisions made by the orthodontist is the exact placement of the brackets on each tooth in order to produce the necessary tooth movement. The computer geometric data base, coupled with the eventual mathematical capabilities of the computer model, will assist in the calculation and display of the exact bracket position on each tooth to produce the required rate, type, and degree of movement. This will allow a more exact functional result to be obtained. This alone will be a major improvement over present methods.

Teaching—The teaching applications of a geometric data base coupled with the visual capabilities of solids modeling are numerous. The ability to rotate geometries in three-dimensional space, to zoom in on areas for emphasis or inspection, and to change the viewing perspective give the instructor a tool that can increase the creativity of teaching methods. Manipulation of the visual display allows the frame of reference of the observer to be readily changed. For example, it is possible to view the lower incisors both from the front and also from the lingual perspective, creating visual impressions not now possible. Automatic teaching and grading of dental technique can also be provided, which will reduce the cost of education, increase the repeatability of grades by eliminating judgments by graders, and give the students the ability to get more practice and feedback when appropriate.

Dentures—It may be possible to replicate soft tissue contours for complete and partial dentures with this digitizing system.

SUMMARY OF THE INVENTION

In view of the foregoing possibilities, the central object of this invention is to develop a mechanical contact digitizer that will enable the geometry of a tooth and its local environment to be digitized before being modeled by a computer.

Another object is to permit the tooth and its local environment to be digitized in a few minutes (less than about 5-10 min.).

A further object is to provide a digitizer whose overall accuracy is less than about 0.025 mm (25 microns).

Yet another object of the invention is to provide a digitizer which can be affixed in the oral cavity by known attachment techniques.

A further object is for the digitizer to have the feel and maneuverability of a dental exploration tool.

Still another object is to provide a digitizer which both is compact enough to fit in the mouth, yet also can be extended to reach all parts of the oral cavity.

A further object is for the digitizer to provide six degrees of freedom for the handpiece, so as to reach any oral surface with the probe tip, from any angle.

Thease and other objects can be achieved, for example by a dental surface tracer including a probe with a tip that can be moved to trace a given dental surface, comprising a mounting device for mounting said tracer to a stable reference location and defining a base plane; a first plurality of links which are substantially coplanar and define a plane of movement; said links being pivotably attached to said mounting device so that said plane of movement makes a variable angle with said base plane; a distal one of said first plurality of links being movable in two dimensions within said plane of movement; means for generating electrical signals representative of movements of said probe tip, as a function exclusively of movements of said first plurality of links; a dental handpiece supporting said probe; and a second plurality of links which hold the handpiece and are attached to said first plurality of links; said second plurality of links holding said probe tip at all times at a fixed location in said plane of movement with respect to said distal link of said first plurality of links; and permitting said handpiece to move about three axes without moving said probe tip from said fixed location. Advantageously, said entire tracer exclusive of said handpiece is sized to be accommodated within the human mouth.

According to another aspect of the invention, a probe system may comprise: a probe; a linking arrangement supporting said probe and having a plurality of joints providing at least 6 degrees of freedom for the probe; a device for attaching said linking arrangement to a stable reference location; and a sensing system which measures all movements of said probe with respect to said reference location; wherein said linking arrangement comprises a first plurality of joints providing three degrees of freedom for said probe, movement of those joints being sensed by said sensing system; and wherein said linking arrangement comprises a second plurality of joints providing said probe with three degrees of freedom independently of said first plurality, movement of said second plurality of joints not being sensed. The attaching device is capable of attaching the linking arrangement to a work bench, or to a reference location on a given jaw.

A gimbal-type arrangement of the second plurality of joints advantageously provides three degrees of freedom for said handpiece while said probe tip remains at the same location with respect to said first through third joints, the probe tip remaining at all times at the common axis of rotation of said fourth, fifth and sixth joints.

The sensing system comprises at least one Hall sensor and at least one magnet associated with said linking arrangement; advantageously first, second and third Hall sensors associated respectively with said first, second and third joints, said first Hall sensor sensing relative movement of said first and second links, said second Hall sensor sensing relative movement of said second and third links, and said third Hall sensor sensing relative movement of said third and fourth links.

Another aspect of the invention relates to linearizing means for receiving output signals from said Hall sensors and improving the linearity thereof.

According to another feature, the invention provides a dental surface tracer including a dental probe having six degrees of freedom, comprising: a mounting device which is capable of being mounted to a reference location with respect to a given jaw and defining a base plane; a first link which is integral with said mounting device; substantially coplanar second, third and fourth links defining a plane of movement; said second link being pivotally mounted to said first link so that said plane of movement is movable above and below said base plane; first means for generating electrical signals representative of such movement; said second, third and fourth links being jointed together to have predetermined ranges of relative angular motion so that a distal end of said fourth link is movable over a predetermined area in said plane of movement; whereby said distal end has three degrees of freedom; second means for generating electrical signals representative of such movement; a probe; and gimbal means supporting said probe and attached to said distal end of said fourth link, for permitting said probe to move with three degrees of freedom without any movement of said first through fourth links; whereby said probe can move with respect to said reference location with six degrees of freedom. All of said links and gimbal means are sized for being accommodated within the human mouth. The second, third and fourth links are jointed to provide greater than 90° of relative angular motion between each pair of adjacent links, or more advantageously, substantially 100° of relative angular motion.

Disclosed herein is a mechanical contact digitizing device which avoids the limitations of the prior art and is, therefore, suitable for the oral and dental environment or the dental lab. A perspective view is shown in FIG. 1. The device is small enough to fit entirely inside the mouth. Such a small size greatly facilitates achieving high accuracy by minimizing the bending of linkages and maximizing the angular motion of the joint motion sensors. The linkages were designed such that they have optimum linear motion to reach all teeth and optimum rotational motion to maneuver the sensor tip to all tooth surfaces. The joint motion sensors are Hall-effect sensors. Every linkage and sensor was designed individually for an accuracy of 0.0025 mm (2.5 microns) in order to achieve an overall digitizer accuracy of less than 25 microns or better. The joints are preloaded to reduce play and increase rigidity. Test data on joint rigidity and Hall-effect joint motion sensor accuracy and hysteresis indicate that an overall digitizer accuracy of less than 25 microns can be achieved.

The disclosed mechanical contact digitizer enables the dentist or the lab to quickly and accurately digitize a tooth or a prepared tooth and its local environment, while at the same time eliminating the need for irritating gingival retraction procedures, because the ball tip of the probe can reach below the gum without retraction. Draws and undercuts can also be detected and measured. Thus, the digitizer provides the dentist with alternatives to the present impression methods.

It is expected that the invention will be used with a suitable computer modeler capable of generation of control data or numerical control commands for controlling automatic machinery associated with the fabrication of a dental restoration. The system in the dentist's office could, for example, carry out the digitizing and then output the geometric data to a floppy disk. This disk would then be sent to a local laboratory for processing and actual construction of the restoration. Alternatively, the data could be sent via other data transmission methods, such as by modem or cable. The local laboratory would have the hardware and software equipment to process this data, develop the computer model, generate the NC interface, and machine the required restoration. This approach has the advantages of effectively complementing the dentist's skills through enhancing accuracy, eliminating the need to use the current impression methods, possibly shortening the time involved for doing the entire restoration, increasing patient comfort, and most importantly, minimizing and substantially eliminating trauma to the gingival tissue. The entire process of making a crown restoration could take less than an hour and it ultimately should be possible to have same-day crown insertion instead of the several days or weeks required with current techniques.

Once tooth geometry, or the entire cavity, has been digitized for computer manipulation, it will be possible to electronically generate all the surface shape information needed to automatically machine tooth replicas, the molds needed for casting study models, or complete restorations. Modeling can be done, for example, using a surface modeling program developed by Prof. E. Dianne Rekow, Associate Professor, School of Dentistry, University of Maryland, and her associates, and described in the U.S. patent applications cross-referenced above. In addition, it will be possible to visually recreate a color-enhanced, three-dimensional computer image. Software for this limited purpose is currently available from Structural Dynamics Research Corp. (SDRC), for example. Manipulation of the image in three dimensions is then possible. The model can be rotated in space, and viewed from all angles. Surfaces can be zoomed in on, allowing different views of different surfaces—the occlusal surface, or the distal or lingual surface of incisors, for example.

An important extension of this work is in the area of structural modeling. Once the geometric data is available it is possible with present software to develop a finite element structural model of either an individual tooth or of the entire set of teeth. Such a finite element model allows stress distributions to be determined and displayed under various loading conditions, leading to new approaches to testing of dental materials, studying the effects of bite dislocations, and determining the proper restorative conditions. The finite element model can be used for the detailed structural design of prosthodontics, including the development of proper material thickness variations for specific loading patterns. This will lead to fewer failures because it will make it possible to determine material placement and tooth preparation based on expected stress levels. New-generation, more-sophisticated testing devices are made possible.

The digital system disclosed here may not necessarily decrease the dentist's required level of skill. It will, however, give the dentist a new tool that offers ease of use, enabling the necessary geometric information to be acquired with greater accuracy and ease.

The digitizing probe is used in the mouth much like an explorer. Alternatively, it can be used on the lab bench. In the mouth, after tooth preparation (without gingival retraction procedures), the digitizer is clamped to a selected tooth or teeth on the same jaw as the tooth preparation and is traced over the prepared surface, following its contour in detail. The process only takes a few minutes and involves very little patient discomfort. The probe tip is placed in contact with the tooth surface, and at a specified frequency or at specified times, data representative of the surface are recorded through the sensing elements in the digitizer linkages. This process will result in sufficient (e.g., several hundred) individual data points representative of the prepared surface geometry. The accuracy of the information will be a function primarily of the apparatus design and will depend little on the dentist's skill in maneuvering the probe on the prepared surface.

The digitizer was designed with the practical needs of the dental practitioner or dental lab in mind. For example, for crown restorations, after tooth preparation (without gingival retraction procedures), the device is temporarily attached to a sound tooth which acts as a jaw-based reference point. The tip of the probe is wiped over the surface of the teeth to be digitized. It will take less than about 3 minutes to digitize a single tooth for crown restorations and less than 15 sec/tooth, or about 8 min. (32 tooth × 0.25 min/tooth) for orthodontic applications, the data being recorded at a rate of several hundred points per second. A minimum of about 400 surface points per tooth is believed necessary for an accuracy of under 25 microns. Direct contact with the surface avoids the problems of translucence and moisture-caused reflection. The ability to fully articulate a very small ball tip (no more than about 0.5 mm) solves the parallax problem by reaching all parts of the tooth, including below the gum line.

One of the fundamental problems in digitizing the oral cavity geometry is the choice of a reference point from which all the spatial coordinate data must be obtained. Preferably, the reference location, with which the device described is best adapted to be used, is another tooth onto which a portion of the measuring device is clamped or temporarily bonded. The reference tooth is rigid with respect to the surfaces being scanned by their common attachment to the jaw. For digitizing the upper teeth the device may be referenced off of one of the upper teeth and for digitizing the lower teeth the device may be referenced off one of the lower teeth, as will be shown and described.

It is contemplated that a complete system for the purpose described above will include the digitizing device generating spatial coordinate data; circuitry for processing the data and supplying it to a floppy disk or other storage or transmission medium; computer modeling, possibly with an expert or CAD system; and for certain applications, machine generation of a restoration or model. The data may be converted to any format for input into modeling software. Any suitable modeling software, including those capable of NC command generation, can be used. A block diagram of such a complete system is shown in FIG. 1A.

Other objects, features and advantages of the invention will be appreciated in view of the following detailed description of an embodiment thereof, with reference to the drawings.

BRIEF DESCRIPTION OF THE DRAWINGS

FIG. 1 is a perspective view of a digitizer;

FIG. 1A is a functional block diagram of an example of a digitizing and data processing system;

FIG. 2 is an elevation of the digitizer, partly in cross-section and partly in phantom;

FIG. 3 is an elevation of the base 1;

FIG. 4 is a view showing the pivot block 2 mounted on the base 1;

FIG. 5 is a plan view showing the frame 7, straight link 8, and dogleg link 9 in their most compact position;

FIG. 6 is a plan view of the frame 7;

FIG. 6A is a side view of the frame 7;

FIGS. 7 and 7A are respectively an elevational and a plan view of the straight link 8;

FIGS. 8, 8A and 8B are respectively a plan view, an elevation, and a cross-section of the dogleg link 9;

FIGS. 9, 9A and 9B show respectively a side view, an end view, and a top view of the first arch 12;

FIGS. 10 and 10A are respectively a side view and a top view of the second arch 13;

FIG. 11 is an elevation of the probe 14;

FIG. 12 is a kinematic diagram showing the range of motion obtainable by certain parts of the digitizer.

DETAILED DESCRIPTION OF AN EMBODIMENT OF THE INVENTION

Figure 13:
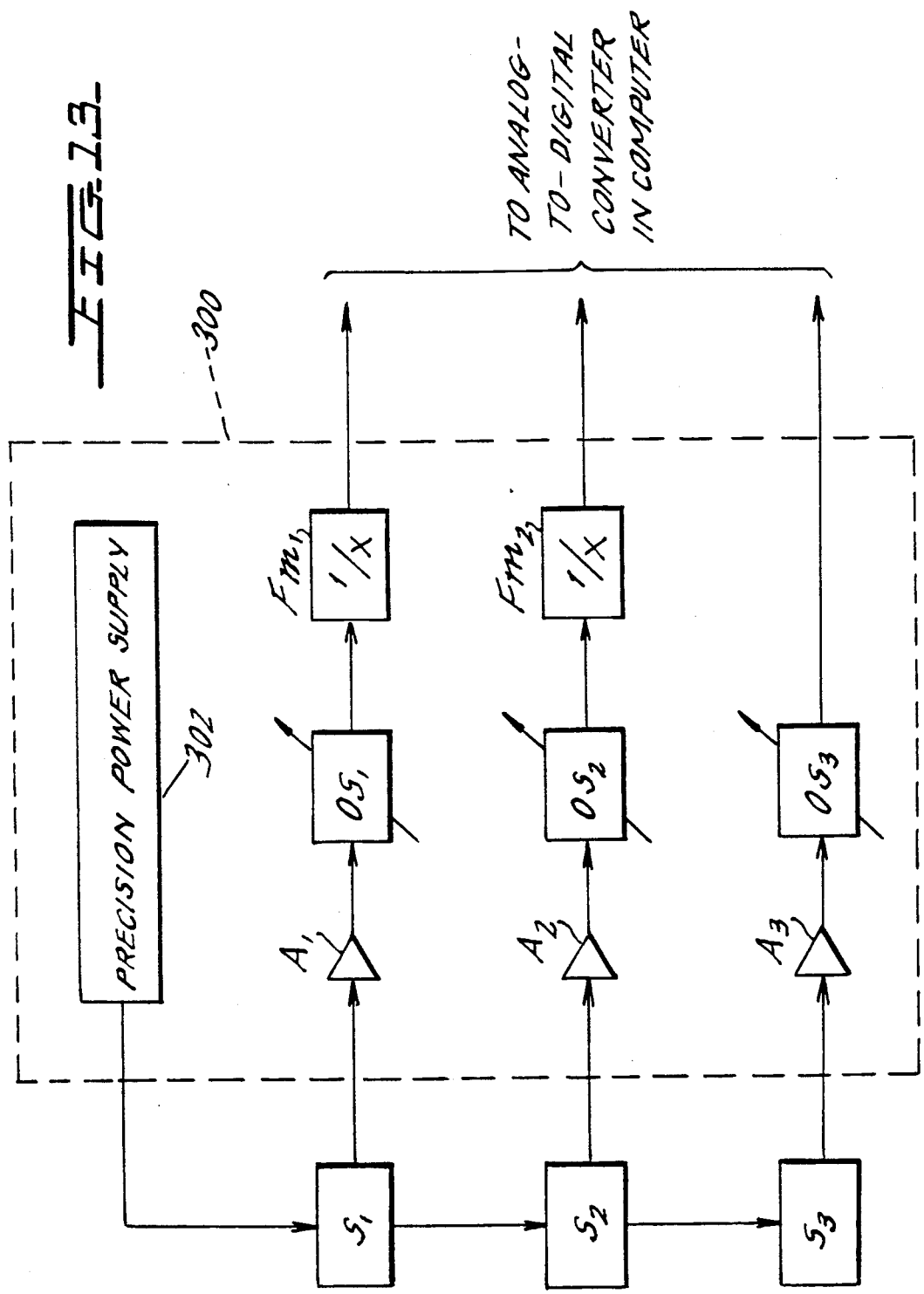
FIG. 13 is a schematic block diagram showing electronic circuitry for conditioning the output signals of the digitizer.

In this disclosure, the terms upper, lower, horizontal, vertical, and the like, are used herein merely as relative terms. No limitation is intended on the position in which the digitizer may be oriented when it is used.

FIG. 1 is a perspective view of the digitizer FIG. 2 is an elevational view of the digitizer, shown partly in cross-section and partly in phantom. It comprises a base 1, a pivot block 2, a frame 7, a straight link 8, a dogleg link 9, a first arch 12, a second arch 13, a probe 14, and a handle 20. A "first joint" is defined between the pivot block 2 and the frame 7, a "second joint" between frame 7 and straight link 8, and so forth. All components are made of a strong, biocompatible material, preferably a metal such as stainless steel. As will be discussed below in more detail, movements of the first through third joints are sensed by Hall-effect sensors. The fourth through sixth joints and their surrounding links form an advantageous gimbal-like arrangement which contributes substantially to the excellent feel and maneuverability of the digitizer. A further advantage of the gimbal is that the position of the probe tip can be continuously sensed without requiring the movement of the fourth through sixth joints to be sensed as well.

FIG. 3 is an elevational view of the base 1. It comprises a crosspiece 101 whose horizontal dimensions are about 0.46 by 0.54 in., a pair of flanges 102 which depend therefrom, and a stem 103 which extends perpendicularly to the crosspiece 101 substantially at its center and is tapered slightly as it extends therefrom. The stem 103 may also be offset from the center of the crosspiece 101 for better access to certain teeth when required. A portion of the outer surface of the stem is surrounded by a dot-dash block 104 in FIG. 3. This is the nominal position of the pivot block 2 which will be mounted thereon.

In FIG. 2, the base 1 is shown mounted on a tooth 105. An adhesive 106 is applied between the base 1 and the tooth 105 to temporarily, but immovably, adhere the base to the tooth. A suitable adhesive typically used by dentists is known as "grey stick compound."

FIG. 4 is a view showing the pivot block 2 mounted on the base 1. See also FIGS. 2 and 5. The pivot block 2 is force-fitted onto the stem 103 of the base 1, via a central bore 107, which is tapered to match the taper of the stem 103. The angle of taper is very small, for example about 3°, and provides a "locking taper." The frame 7 is pivotable about the pivot block 2 in the plane of the drawing as shown in FIG. 2.

Bearings 5 are mounted in frame 7 in a pair of apertures 116, as shown in FIGS. 4, 5, 6, and 6A. All bearings in the digitizer are preferably ball bearings which are preloaded, i.e., forces are applied to the balls even when the digitizer itself is not bearing any load. Preloading the bearings is preferable so as to increase rigidity by reducing play. The construction of preloaded bearings is in itself known of the art, although not in conjunction with the other inventive features disclosed herein.

In the frame 7, the bearings 5 receive a pair of tapered projections 110 on an outer surface of the pivot block 2 Thus, the frame 7 is pivotable with respect to the pivot block 2. As shown in FIG. 2 in phantom, advantageously the available pivot angle is at least 15° above and below the horizontal, as defined by the cross piece 101 of the base 1. Note in FIG. 2 that the frame 7, the straight link 8 and the dogleg link 9 are joined so as to pivot together as a unit through the entire 30° range of motion with respect to the pivot block 2.

FIG. 6 shows a plan view of the frame 7. The frame 7 has a generally flat, plate-like shape, substantially 0.25 inch thick. A large aperture 112 is formed at one end, and shaped for being freely assembled over the pivot block 2. A cutout lengthwise surface 113 is formed along one side of the frame 7. At the end of the frame 7 opposite the aperture 112 and adjacent the cutout surface 113 is a bearing hole 114, which is formed in a portion of the frame 7 projecting generally perpendicularly to the cutout surface 113 and in the same plane. The frame is substantially 0.896 inch from the end 116a to the center of the hole 114.

Substantially a 40° angle is formed between the cutout surface 113 and the lengthwise inner surface 112a of the aperture 112. Substantially a 50° angle is formed between the surface 112a and an extension 113a of the surface 113, which is offset substantially 10° from the surface 113. The lengthwise surface 115 is offset substantially 10°30' from the surface 112a. The bearings 5 shown schematically in FIG. 6 are held in the frame 7 by adhesive. As shown in FIG. 6A, a side view of the frame 7, the second end 117 in which the bearing hole 114 is formed, comprises an upper part 117a (with a hole 114a) and a lower part 117b (with a hole 114b) which are parallel and form a fork. As shown schematically in FIG. 6A, bearings 5, preferably ball-bearings, are respectively secured in the upper and lower parts 117a, 117b by adhesive.

The straight link 8 is shown in elevation in FIG. 7. A plan view is seen in FIG. 7A. The straight link 8 has a first end 123 and a second end 124. Upper and lower surfaces of the link 8 may be flat and parallel. The link 8 is thicker, substantially 0.25 inch, at a central portion 125 than at the ends 123, 124 (substantially 0.116 inch). The link 8 is substantially 0.5 inch between the centers of holes 126, 128, and 0.7 inch overall.

The first end 123 is sized to fit closely between the upper and lower parts 117a, 117b of the second end 117 of the frame 7. A suitable shaft is inserted in a vertically extending bore 126 and secured by a set screw 11 or the like for engaging the bearings 5 in the second end 117 of the frame 7.

The link 8 is substantially constant in width (0.1875 inch), as seen in FIG. 7A. The first end 123 has a substantially circular rounded outline. The second end 124 is substantially circularly rounded on one lateral side, but has a flattened part 127 which in this example forms substantially an 80° angle with the adjacent lateral side. The second end 124 also has a bore 128 which receives a suitable shaft which will be discussed below.

Extending from side to side of the link 8, substantially midway between its top and bottom surfaces, is an oblique bore 129. It is substantially circular in cross-section in this example and its cylindrical walls form substantially a 64° angle with the lateral sides of the link 8.

FIGS. 8, 8A and 8B are respectively a plan view, an elevational view, and a cross-sectional view of a dogleg link 9. The cross-sectional view of FIG. 8B is taken along the line 8B—8B in FIG. 8A. The link 9 has a first end 140 and a second end 141. The first end 140 has an upper part and a lower part 140a, 140b which are parallel and form a fork configuration to engage the second end 124 of the straight link 8. A mounting hole 142 comprising an upper part 142a and a lower part 142b registers with the bore 128 in the link 8. Respective bearings 5 are provided in the upper and lower holes 142a, 142b and retain a shaft (not shown) which is secured in the bore 128 by setscrews 11 or the like.

The dogleg link 9 has a pair of lateral walls 143, 144 which define a longitudinal direction. The first end 140 has a first outer wall 145 which extends at substantially a 30° angle to the longitudinal direction. A second outer wall 146 extends at substantially a 50° angle to the longitudinal direction. An inner wall 147 extends at substantially a 50° angle to the longitudinal direction. An end wall 148 forms a substantially 50° angle to the longitudinal direction and forms a 100° angle with both the second outer wall 146 and the inner wall 147.

A second inner wall 149 extends at substantially a 40° angle to the longitudinal direction and accordingly, a 90° angle to the first inner wall 147. It extends inward from the lateral wall 144. The surfaces of the second outer wall 146 and the end wall 148 are substantially flat and form a corner. The first end 140 is rounded between the end wall 148 and the first inner wall 147, preferably circularly A cutout 155 extends from the top surface. At its lateral walls the cutout is defined by a pair of shoulders 156. The bottom wall within the cutout 155 is formed with substantially flat portions 157 adjacent the shoulders 156 and a central rounded portion 158. Preferably the flat portions 155 form substantially a 45° angle with the horizontal. The rounded portion 158 is preferably cylindrical having an axis extending in the longitudinal direction of the link 9.

The second end 141 has an end wall 160. A bore 161 is formed, preferably coaxially with the axis of the rounded portion 158 and extends longitudinally through the end wall 160, past the cutout 155 and then extends further, into the body of the link 9.

The link 9 measures substantially 0.330 inch overall in the transverse direction and is substantially 0.725 inch from the end wall 160 to the center of hole 142.

A side view, an end view, and a top view of the first arch 12 are shown in FIGS. 9, 9A and 9B, respectively. The first arch 12 has a first end 164 and a second end 165. The first end 164 has a rounded surface 166, preferably cylindrical, which is configured to match the rounded portion 158 in the cutout 155 of the dogleg link 9. A bore 167 receives a pin which engages the bearings 5 on either side of the cutout 155. The pin (not shown) is secured to the first end 164 by set screws provided in a pair of suitable bores 11. Extending upward from the first end 166 the arch 12 curves by 90° and reaches the second end 165. The second end 165 has an upper portion and a lower portion which are parallel and have respective holes 172a and 172b which together define a bore 172. The holes 172a and 172b have respective bearings 5. A pair of angle walls 173a, 173b are formed in the arch 12 and define a space within the fork 165a, 165b at the end thereof away from the second end 165. The angle walls each form substantially a 45° angle to the longitudinal sides of the arch 12 and thereby form a substantially 90° angle to each other. Advantageously, the junction between the two angle walls may be broken to form a short flat portion 174 which is perpendicular to the longitudinal direction of the arch 12. The arch 12 measures substantially 0.666 inch horizontally from the end 164 to the center of hole 172.

The second arch 13 is shown in side view in FIG. 10 and a top view is shown in FIG. 10A. Starting from a first end 180 the second arch curves through 90° and ends with a second end 181. A tongue portion 182 has a vertical bore 183 therein. With the tongue portion 182 inserted into the aperture 175 of the first arch 12, a pin 16 (FIG. 2) can be secured within the bore 193 by a set screw at 11 and rotatably supported in the bearings 5 of the second end 165 of the first arch 12.

Two pairs of angle walls 184a, 184b, 184c, 184d are formed at the end of the tongue portion 182 away from the first end 180. The angle walls 184a, 184b are above the tongue portion 182 and the angle walls 184c (not shown) and 184d are below the tongue portion 182. Preferably a small flat part 185 is formed at the junction between each pair of angle walls. A 90° angle is formed between each pair of angle walls and each angle wall forms a substantially 45° angle to the longitudinal direction of the arch 13. The arch 13 measures substantially 1.245 inch horizontally from the second end 181 to the center of the bore 183.

As shown and described, the elements are small, but are large in cross-section. Their large cross-section prevents bending from the torque in the bearings and from gravity, yielding high accuracy. The joints employ miniature ball bearings, preloaded to produce low bending torques, and motion without bearing play.

The probe 14 is shown in FIG. 11. As shown in the assembly view in FIG. 2, a pair of sets of bearings 186 are mounted via retaining rings 185 in a pair of circumferential grooves 187 formed in the bore 188 in the second end 181 of the second arch 13.

The probe 14 is substantially straight over about ⅝ of its length. It is threaded at a first end 192 The second end 193 is generally C-shaped. At its second end it has a probe tip 194 which is advantageously a ball having a diameter of about 0.5 mm. The contact tip advantageously is less than or equal to 0.5 mm in diameter, to minimize interference with gums and neighboring teeth. Advantageously, the curved second end 193 extends substantially perpendicularly at 193a to the shaft 192a, then at 193b runs parallel to the shaft, and then at 193c forms an angle of substantially 65° to the shaft. The section 193c advantageously tapers to define an included angle of substantially 16°, so as to be smaller than the tip 194 at the point of attachment, but to increase rapidly in thickness so as to maintain the stiffness of the probe. The overall length of the probe 14 is substantially 1.70 inch.

The probe 14 is rotatably held in the bore 188 of the second arch 13 by a retaining ring 195 in a groove 196, and a shim 197 of a suitable thickness between the retaining ring 195 and the first end 181 of the arch 13. The probe tip 194 is oriented such that it is coaxial with the shaft 192a of the probe 14, coaxial with the bores 172, 183 in the first and second arches 12, 13, and coaxial with the bore 161 in the dogleg link 9. By these features, the dogleg link 9 and the arches 12, 13 form the highly advantageous gimbal-like arrangement mentioned above.

The dogleg link 9, the straight link 8 and the frame 7 are configured for being joined by pins inserted through the bores 126, 128 in the link 8. When thus joined, as best seen in FIG. 1, the link 9 can be extended toward and away from the frame 7 while the frame 7 and the links 8 and 9 remain in the same plane. In other words, the frame 7 and the links 8 and 9 pivot as a unit through an angle of substantially 15° above and below the horizontal, with respect to the pivot block 2.

The link 8 is shaped to fit compactly between the frame 7 and the link 9 when the latter are in their least extended position, as shown in FIG. 5. Note that in this position, the circularly rounded end 123 of the straight link 8 abuts the surface 113 of the frame 7 and in parallel therewith. Also in this position, the end wall 148 of the dogleg link 9 is angled so as to abut the 10° offset extension 113a of the frame 7. On the other hand, the rounded part of the second end 124 of the link 8 abuts the frame 7, while the flattened part 127 of the second end 124 projects outward away from the frame 7.

FIG. 12 is a kinematic diagram showing the substantial range of motion obtainable by the arrangement of the frame 7, the link 8 and the link 9. In FIG. 12, alpha represents the rotation of the straight link 8 with respect to the frame 7, while beta represents the rotation of the dogleg link 9 with respect to the straight link 8. Reference numerals 126a, 126b and 126c show the position of the bore 126 when alpha equals 0°, 3° and 100°, respectively. Reference numeral 128a indicates the position of the bore 128. A, B, C and D indicate the location of a distal end of the dogleg link 9 for various values of alpha and beta, which are shown in the drawing.

For example, starting from the least extended position shown in FIG. 5, the link 9 can be rotated throughout a wide angle beta of substantially 100°, which is limited by surface 148 on link 9 contacting surface 125a on the central portion 125 of link 8. As beta approaches 100°, an interference occurs between the end wall 148 and the extension 113a, whereby alpha is constrained to have a minimum value of 3° when beta equals 100°. A line 9' in FIG. 12 indicates a theoretical position the link 9 would take if alpha were 0°.

The value of alpha is limited to 100° by the flattened part 127 on the second end 124 of the link 8, which comes into contact with a vertical side wall of the frame 7 when alpha reaches 100°.

As shown in FIG. 2, a handpiece (handle) 20 comprising a tube 21, a distal end piece 22 and a proximal end piece 23 is firmly connected to the first end 192 of the probe by the threads which are formed there. The connection is also secured by set screws at 11.

As thus disclosed and described, the disclosed arrangement provides six degrees of freedom for the digitizer. The probe 14 is rotatable 360° by its handpiece 20 about its axis, journalled within the first end of the second arch 13. While it is rotated, its probe tip remains at the axis of the pivot pin 16 between the first arch 12 and the second arch 13.

The first arch 12 can pivot with respect to the arch 13 at the pivot point provided therebetween.

Because of the angle walls formed at a 45° angle in each of the arches, each of the arches can pivot substantially 135° out of the plane shown in FIG. 2. In other words, taking the position of FIG. 2 as a starting point, with the arch 12 held stationary, the arch 13 can be pivoted 135° out of that plane in either direction. Throughout this pivoting motion, the probe tip 194 remains at the axis of the pivot pin 16 between the arches 12, 13 and at the axis of the bore 167 in the first end 164 of the arch 12.

The arch 12 is also pivotable about the pivot pin 15 within the cutout 155 in the dogleg link 9. Because of the flat portions 157 within the cutout 155, and the corresponding side surfaces of the first end of the arch 12, the arch 12 can pivot substantially 45° in either direction about the pivot pin 15. Throughout the pivoting of the arch 12 within the cutout 155, the probe tip 194 remains concentric with the axis of the pivot pin 15.

The extension and pivoting motion of the link 9, the link 8 and the frame 7 has already been discussed. In addition, the frame 7 can pivot as shown in FIG. 2 substantially at least 15° above and below the horizontal, about the bearings 5 of the pivot block 2. This linkage enables the probe tip to reach any portion of any tooth in the patient's mouth.

By this arrangement, the tip 194 is movable only with respect to the first, second and third joints, not the fourth through sixth joints.

Also, the gimbal-like arrangement of the fourth through sixth joints, plus the spatial motion provided by joints one through three, allows the entire load of the user's hand to pass to the tip, thereby isolating all six joints from the hand load. This makes it possible, if desired, to employ a tip pressure sensor (not shown) to control when sensor readings should begin.

It should be noted that the disclosed gimbal arrangement is not the only possible way to isolate the first three joints from the hand load; such a result can be provided, for example, by other six-degree-of-freedom linkages.

Sensors

The angular motion of each of the first three joints is measured magnetically, using Hall-effect sensors, which advantageously do not apply friction or torque loads to the joints.

As is well known, each Hall sensor produces a variable voltage as a function of the magnetic flux from the corresponding magnet.

The substantially 100° range of the angular motion of the second and third joints allows the Hall-effect sensors to detect this angular motion with great resolution. Because the digitizer links are very small, even a small movement of the probe tip results in a substantial angular movement of the joints. This combination of the small size of the links, and the resolution of the angular motion sensors, gives the probe great precision in the measurement of small distances.

The positions of the various elements with respect to each other are converted into electrical signals by a plurality of magnets and a corresponding plurality of Hall-effect sensors mounted on the various components.

A small NdFe horseshoe magnet 3 is mounted on the inner body 111 of the pivot block 2 and a corresponding Hall sensor 4a is mounted facing the magnet 3 on an inner surface of the frame 7 (FIG. 2). The horseshoe magnet creates an intense but highly concentrated magnetic field near its poles which can be sensed by Hall sensor 4a which is close to it, but not by the Hall sensors 4b, 4c on frame 7 and link 9, which are substantially farther away.

An elongated NdFe magnet 10 is located in the bore 129 in the straight link 8 (FIG. 7a) and confronts respective Hall sensors 4b, 4c on the cutout surface 113 of the frame 7 and the second inner wall 149 of the link 9 (FIG. 5). By this arrangement of a single bar magnet between the two Hall sensors, plus the limitation on the values of the rotation angles alpha and beta, advantageously 100°, substantial interaction of the two sensing axes is avoided.

The Hall sensors and the materials of their corresponding links are advantageously made of nonmagnetic materials, the links being nonmagnetic stainless steel in this case. Therefore, the relative motions of the links have negligible effect on the large field pattern of the bar magnet 10. Because of the large field pattern of the bar magnet 10, motion of link 8 which holds the magnet does produce an unwanted magnetic field change at Hall sensor 4a. Advantageously, however, sensor 4a is monitored at low amplification, because greater amplification is not necessary to measure the large magnetic field changes of the intense horseshoe magnet field. Therefore the small field changes at 4a from the bar magnet 10 are insignificant. By this method all three joint motions can be measured independently.

Electronics

Referring now to FIG. 13, the Hall sensors $S_1$, $S_2$ and $S_3$ are supplied with a constant reference current by a precision power supply 302 in an electronic assembly 300. $S_1$ is the sensor closest to the third joint, while $S_3$ is the sensor between the frame 7 and the pivot block 2. The signals from the Hall sensors are initially conditioned by corresponding low-noise amplifiers $A_1$, $A_2$, and $A_3$ which amplify the sensor output voltages to the range of 1 to 10 V as required by further analog functional modules in this embodiment of the invention. The gain of the amplifiers is about 50. Then corresponding offset adjustment modules $OS_1$, $OS_2$, and $OS_3$ remove the constant sensor bias voltage.

The output voltage of a Hall sensor generally does not vary linearly with the distance from a magnet, but rather the voltage varies as the reciprocal of the distance. Accordingly, for the sensors associated with the second and third joints, the relationship between the sensor output voltage and the link angle is substantially linearized by analog function modules $FM_1$ and $FM_2$ wherein the output is the reciprocal of the input. This processing advantageously provides adequate and uniform resolution over the whole range of motion of the second and third joints.

Linearizing is not necessary for the sensor of the first joint, because as shown in FIG. 2, its magnet is a horseshoe magnet and the sensor has a small range of motion essentially limited to between the north and south poles. Because of this arrangement, the output of $S_3$ is already substantially linear.

After processing, all three signals can be supplied to a conventional plug-in A/D board for an IBM-compatible personal computer, such as the Data Translation DT2808, for further analysis.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A probe system comprising:
   a probe;
   a linking arrangement supporting said probe and having a plurality of joints providing at least 6 degrees of freedom for the probe;
   a device for attaching said linking arrangement to a stable reference location; and
   a sensing system which measures all movements of said probe with respect to said reference location;
   wherein said linking arrangement comprises a first plurality of joints providing three degrees of freedom for said probe, movement of those joints being sensed by said sensing system; and
   wherein said linking arrangement comprises a second plurality of joints providing said probe with three degrees of freedom independently of said first plurality, movement of said second plurality of joints not being sensed.

2. A system as in claim 1, wherein said attaching device is capable of attaching the linking arrangement to a work bench.

3. A system as in claim 1, wherein said probe system is for scanning dental surfaces; said attaching device is capable of attaching the linking arrangement to a reference location on a given jaw; and said probe is movable to completely scan a predetermined dental surface on said given jaw.

4. A system as in claim 3, further comprising an adhesive which adheres said attaching device to said reference location.

5. A system as in claim 3, further comprising a handpiece which is firmly attached to said probe.

6. A system as in claim 5, wherein said probe has a curved shank extending from said handpiece and a tip at a distal end of said shank.

7. A system as in claim 6, wherein said curved shank is shaped so as to permit convenient access to all portions of such dental surface.

8. A system as in claim 7, wherein said distal end of said curved shank defines an angle with respect to said handpiece, which angle is selected to permit the distal end of the shank to be perpendicular to the plane of a given jaw while the handpiece extends away from the jaw, remaining clear of the teeth of the jaw.

9. A system as in claim 7, wherein said linking arrangement comprises at least first through sixth links which define at least first through fifth joints in that order, and a sixth joint is defined between said sixth link and the combination of said probe and handpiece.

10. A system as in claim 9, wherein said second, third and fourth links are substantially coplanar.

11. A system as in claim 10, wherein said fourth, fifth, and sixth joints form gimbal means permitting movement of said handpiece while said probe tip and said first through third joints remain in the same position.

12. A system as in claim 11, wherein said gimbal means provides three degrees of freedom for said handpiece and permits rotation of said probe tip while said probe tip remains at the same location with respect to said first through third joints.

13. A system as in claim 12, wherein said sixth joint is a journal which permits the probe to rotate about its longitudinal axis with respect to said sixth link.

14. A system as in claim 11, wherein said fourth and fifth joints are swivel joints each having an axis of rotation.

15. A system as in claim 14, wherein said probe tip remains at all times at the common axis of rotation of said fourth, fifth and sixth joints.

16. A system as in claim 15, wherein said sensing system comprises at least one Hall sensor and at least one magnet associated with said linking arrangement.

17. A system as in claim 15, wherein said sensing means comprises a Hall affect sensor system associated with said first, second and third joints.

18. A system as in claim 17, comprising first, second and third Hall sensors associated respectively with said first, second and third joints, said first Hall sensor sensing relative movement of said first and second links, said second Hall sensor sensing relative movement of said second and third links, and said third Hall sensor sensing relative movement of said third and fourth links.

19. A system as in claim 18, further comprising an elongated magnet on said third link and operatively associated with both said second and third Hall sensors, which are respectively on said second and fourth links.

20. A system as in claim 19, further comprising a horseshoe magnet operatively associated with said first Hall sensor.

21. A system as in claim 18, further comprising linearizing means for receiving output signals from said Hall sensors and improving the linearity thereof.

22. A system as in claim 3, wherein said sensing system has means for generating electrical signals representative of said movements of said probe.

23. A dental surface tracer including a dental probe having six degrees of freedom, comprising:
  a mounting device which is capable of being mounted to a reference location with respect to a given jaw and defining a base plane;
  a first link which is integral with said mounting device;
  substantially coplanar second, third and fourth links defining a plane of movement; said second link being pivotally mounted to said first link so that said plane of movement is movable above and below said base plane; first means for generating electrical signals representative of such movement; said second, third and fourth links being jointed together to have predetermined ranges of relative angular motion so that a distal end of said fourth link is movable over a predetermined area in said plane of movement; whereby said distal end has three degrees of freedom; second means for generating electrical signals representative of such movement;
  a probe; and
  gimbal means supporting said probe and attached to said distal end of said fourth link, for permitting said probe to move with three degrees of freedom without any movement of said first through fourth links;
  whereby said probe can move with respect to said reference location with six degrees of freedom.

24. A tracer as in claim 23, wherein all of said links and gimbal means are sized for being accommodated within the human mouth.

25. A tracer as in claim 24, wherein said second, third and fourth links are jointed to provide greater than 90° of relative angular motion between each pair of adjacent links.

26. A tracer as in claim 25, wherein substantially 100° of relative angular motion is provided.

27. A tracer as in claim 23, wherein said probe has a tip for tracing a desired dental surface on said jaw, and said first and second means generate electrical signals representative of movement of said probe tip on said dental surface.

28. A tracer as in claim 27, wherein said gimbal means permit rotation of said probe tip within said plane of movement without any movement of said first through fourth links.

29. A tracer as in claim 28, wherein said probe tip remains at all times at the same location with respect to said first through fourth links.

30. A dental surface tracer including a probe with a tip that can be moved to trace a given dental surface, comprising:
  a mounting device for mounting said tracer to a stable reference location and defining a base plane;
  a first plurality of links which are substantially coplanar and define a plane of movement; said links being pivotably attached to said mounting device so that said plane of movement makes a variable angle with said base plane; a distal one of said first plurality of links being movable in two dimensions within said plane of movement;
  means for generating electrical signals representative of movements of said probe tip, as a function exclusively of movements of said first plurality of links;
  a dental handpiece supporting said probe; and
  a second plurality of links which hold the handpiece and are attached to said first plurality of links;
  said second plurality of links holding said probe tip at all times at a fixed location in said plane of movement with respect to said distal link of said first plurality of links; and permitting said handpiece to move about three axes without moving said probe tip from said fixed location.

31. A tracer as in claim 30, wherein said entire tracer exclusive of said handpiece is sized to be accommodated within the human mouth.

* * * * *